United States Patent [19]  
Pierce

[11] 4,067,896  
[45] Jan. 10, 1978

[54] (ISOTHIOCYANATO-METHOXY) BIPHENYLS

[75] Inventor: James K. Pierce, Midland, Mich.

[73] Assignee: The Dow Chemical Company, Midland, Mich.

[21] Appl. No.: 742,038

[22] Filed: Nov. 15, 1976

[51] Int. Cl.$^2$ .................. A01N 9/18; C07C 161/04
[52] U.S. Cl. ............................ 260/454; 71/104; 424/302
[58] Field of Search ........................... 260/454

[56] References Cited

U.S. PATENT DOCUMENTS

| 2,850,524 | 9/1958 | Mowry et al. | 260/454 |
| 3,085,045 | 4/1963 | Lukes et al. | 260/454 |

FOREIGN PATENT DOCUMENTS 825,693 12/1959 United Kingdom.

Primary Examiner—Joseph Paul Brust  
Assistant Examiner—Robert C. Whittenbaugh  
Attorney, Agent, or Firm—Daniel L. De Joseph; C. Kenneth Bjork

[57] ABSTRACT (Isothiocyanatomethoxy)-1,1'-biphenyl compounds are disclosed. These compounds have utility as antimicrobials, herbicides, fungicides, and insecticides.

15 Claims, No Drawings

(ISOTHIOCYANATO-METHOXY) BIPHENYLS

BACKGROUND OF THE INVENTION

It is known in the art to utilize organic isothiocyanates as a means of inhibiting or otherwise controlling the growth of microorganisms such as those of the type exemplified by fungi, bacteria and the like. For instance, methylisothiocyanate is a toxicant commonly used for this purpose.

Benzal isothiocyanate has been proposed as a fungicide and, in this connection, reference is made to British Pat. No. 825,693. U.S. Pat. No. 3,085,045 teaches phenylmercaptoalkyl isothiocyanate compounds as antimicrobials, but does not teach or disclose biphenyl isothiocyanates.

SUMMARY OF THE INVENTION

The novel compounds of this invention are (isothiocyanatomethoxy)-1,1'-biphenyl compounds of the formula

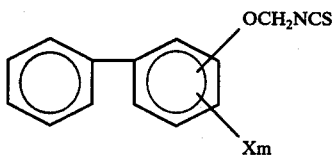

wherein
X represents Cl, Br, F, $OCH_3$, $NO_2$ or an alkyl group having one to four carbon atoms, and
m is an integer having a value of 0, 1, 2, 3 or 4. These compounds have utility as antimicrobials, herbicides, fungicides, and insecticides.

Representative compounds of the invention include:
2-(Isothiocyanatomethoxy)-1,1'-biphenyl;
3-(Isothiocyanatomethoxy)-1,1'-biphenyl;
4-(Isothiocyanatomethoxy)-1,1'-biphenyl;
2-Chloro-4-(isothiocyanatomethoxy)-1,1'-biphenyl;
3-Chloro-4-(isothiocyanatomethoxy)-1,1'-biphenyl;
5-Chloro-2-(isothiocyanatomethoxy)-1,1'-biphenyl;
3-Fluoro-4-(isothiocyanatomethoxy)-1,1'-biphenyl;
5-Chloro-3-(isothiocyanatomethoxy)-1,1'-biphenyl;
3-Methyl-4-(isothiocyanatomethoxy)-1,1'-biphenyl;
2-Fluoro-4-(isothiocyanatomethoxy)-1,1'-biphenyl;
2,6-Dichloro-4-(isothiocyanatomethoxy)-1,1'-biphenyl;
2-Methyl-4-(isothiocyanatomethoxy)-1,1'-biphenyl;
2,6-Difluoro-4-(isothiocyanatomethoxy)-1,1'-biphenyl;
2-Ethyl-4-(isothiocyanatomethoxy)-1,1'-biphenyl;
2,6-Dimethyl-4-(isothiocyanatomethoxy)-1,1'-biphenyl;
3-Chloro-2-(isothiocyanatomethoxy)-1,1'-biphenyl;
3-Fluoro-2-(isothiocyanatomethoxy)-1,1'-biphenyl;
3-Propyl-4-(isothiocyanatomethoxy)-1,1'-biphenyl;
2-Bromo-4-(isothiocyanatomethoxy)-1,1'-biphenyl;
2,6-Dibromo-4-(isothiocyanatomethoxy)-1,1'-biphenyl;
2-Chloro-3-(isothiocyanatomethoxy)-1,1'-biphenyl;
2-Ethyl-3-(isothiocyanatomethoxy)-1,1'-biphenyl;
3-Methoxy-4-(isothiocyanatomethoxy)-1,1'-biphenyl;
2,5,6-Trifluoro-4-(isothiocyanatomethoxy)-1,1-biphenyl;
2,5,6-Trichloro-4-(isothiocyanatomethoxy)-1,1-biphenyl; and
2-Methoxy-4-(isothiocyanatomethoxy)-1,1'-biphenyl.

The novel (isothiocyanatomethoxy) biphenyl compounds of the present invention are prepared in a two step process from the corresponding (chloromethoxy)-1,1-biphenyl compounds which in turn are prepared from the corresponding methoxy-1,1'-biphenyl compounds.

In the first step of the process, the desired (chloromethoxy)-1,1'-biphenyl intermediate compound is produced by slowly adding a solution of substantially one molar proportion of sulfuryl chloride in an appropriate polar organic solvent such as, for example, carbon tetrachloride, to substantially one molar proportion of the corresponding methoxy-1,1'-biphenyl which is being heated at reflux in a similar solvent, preferably in the presence of actinic radiation. After the addition is complete, the reaction medium is heated at reflux for from about 1 hour to about 10 hours and then slowly cooled. The solvent is removed, such as by evaporation, and the desired (chloromethoxy)-1,1'-biphenyl compound is recovered from the residue by distillation or other conventional separatory techniques.

In the second step of the process, substantially one molar proportion of potassium thiocyanate is reacted with substantially one molar proportion of the intermediate chloromethoxy-1,1'-biphenyl which is in a suitable solvent, such as acetone or dimethylsulfoxide. The mixture is stirred and refluxed for from about 0.5 to about 6 hours, diluted with water, and extracted, such as with ether. After drying and concentrating the extracts the desired (isothiocyanatomethoxy)-1,1'-biphenyl is recovered by distillation or other conventional separatory techniques.

The following example illustrates the present invention and the manner by which it can be practiced but as such should not be construed as a limitation upon the overall scope of the same. The intermediate and product compounds are identified by elemental analysis and nuclear magnetic resonance spectroscopy.

EXAMPLE

A solution of 75.0 g (0.407 mole) of 2-methoxy-1,1'-biphenyl in 400 ml carbon tetrachloride was heated to reflux and illuminated with a sunlamp. To this solution was added, over a period of 1 hour, 54.94 g (0.407 mole) of sulfuryl chloride in 300 ml carbon tetrachloride. After addition was complete, the solution was refluxed for three hours, whereupon it was allowed to cool and the solvent was removed by evaporation. The residue was distilled in vacuo to give 65.09 g (0.297 mole) of a colorless liquid, which was identified as the desired intermediate 2-(chloromethoxy)-1,1'-biphenyl.

Twenty grams (0.091 mole) of 2-(chloromethoxy)-1,1'-biphenyl was thereafter dissolved in 200 ml anhydrous acetone. To this solution was added 9.72 g (0.100 mole) potassium thiocyanate. The resulting mixture was stirred and refluxed for 6.5 hours, whereupon it was diluted with 500 ml ice water and extracted with ether. The extracts were dried with $MgSO_4$ and concentrated to give an orange oil which was distilled in vacuo to give 14.32 g of 2-(isothiocyanatomethoxy)-1,1'-biphenyl as a pale yellow oil, boiling at 169°-171° C at 1.0 mm pressure.

Analysis — Calculated for $C_{14}H_{11}NOS$: C, 69.68; H, 4.60; N, 5.80. Found: C, 70.80; H, 4.79; N, 5.36.

The (isothiocyanatomethoxy)-1,1'-biphenyl compounds of the invention are useful as antimicrobial agents for the control of bacteria and fungi. This is not to suggest that these compounds and mixtures thereof with usual additives are equally effective against all such organisms at the same concentration. For such uses, these compounds can be employed in an unmodified form or in the form of a liquid or finely-divided solid composition. Thus, the compounds can be dispersed in a finely-divided solid and employed as a dust. Such mixtures can also be dispersed in water with the aid of a surface-active agent and the resulting emulsion employed as a spray. In other procedures, the isothiocyanatomethoxy biphenyl compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 50 to about 500 parts by weight of one or more of the compounds per million parts of such compositions.

In representative activity tests, 2-(isothiocyanatomethoxy)-1,1'-biphenyl (Compound A), 4-(isothiocyanatomethoxy)-1,1'-biphenyl (Compound B), and 3-chloro-4-(isothiocyanatomethoxy)-1,1'-biphenyl (Compound C) were separately dispersed in warm melted nutrient agar which was then poured into petri dishes and allowed to solidify, the (isothiocyanatomethoxy)-1,1'-biphenyl compounds being employed in an amount sufficient to provide from 5 to 500 parts by weight thereof per million parts (ppm) of the ultimate agar composition. The surface of the agar was then inoculated with a variety of bacterial and fungal pest organisms, and the inoculated plates were incubated under conditions conducive to bacterial and fungal growth. Similar check plates in which the agar contains no active (isothiocyanatomethoxy)-1,1'-biphenyl or other toxic compounds were similarly inoculated and incubated.

In such operations, Compounds A, B, and C gave 100% growth inhibition (kills) and control of the following organisms at the indicated concentrations in parts per million:

TABLE 1

| | Antimicrobial Activity | | |
|---|---|---|---|
| Organism | Compound A (Conc. in ppm) | Compound B (Conc. in ppm) | Compound C (Conc. in ppm) |
| S. aureus | 100 | 50 | 50 |
| B. subtilis | 100 | 50 | 10 |
| C. albicans | 100 | 50 | 10 |
| C. pelliculosa | 100 | 50 | 50 |
| Ceratocystis ips | 100 | 5 | 5 |
| T. mentagrophytes | 100 | 5 | 5 |
| A. niger | 100 | 50 | 50 |

Compounds of the present invention have also displayed utility as herbicides, insecticides, and foliar fungicides. The compounds can be employed as pesticides by distributing the compound, in a pesticidally effective quantity and usually in the form of a composition containing adjuvants to aid in dispersing the same, so as to contact directly the plant or other organism to be controlled, or, alternatively, so as to contact the growth medium or habitat of the organisms whereby eventual contact with said organisms will be established. For the control of weeds and other higher plant pests, the organisms are contacted with a pesticidal amount which is also a herbicidal amount of the compound. Thus, many weed pests are controlled by the distribution in soil of from about 2 to 10 pounds or more of the chemical per acre so as to contact seeds and emerging seedlings of the vegetation to be controlled. For the control of bacterial and fungal pests, including those forms occurring in various paint, paper pulp and wood impregnating formulations, the active chemicals are applied in the form of compositions containing from 50 to 500 or more parts of the chemical per million parts by weight of the composition. For example, in post-emergent herbicide operations, Compound A exhibited 100% kill of pigweeds, and 80% kill of yellow foxtail and morning glory when contacted therewith with compositions that contained the active compound at a concentration of 4,000 parts by weight of the compound per million parts by weight of the ultimate dispersion. In insecticidal operations, Compound A exhibited 100% kill and control of the two-spotted spider mite at a concentration of 100 ppm and 100% kill and control of the western-spotted cucumber beetle larvae at a concentration of 25 ppm. Both Compound B and Compound C exhibited 100% kill and control of the beet army worm larvae at a concentration of 400 ppm. In foliar fungicide operations, Compound A gave 100% kill and control and both Compound B and Compound C gave 95% kill of apple scab fungus on apple trees when employed as aqueous foliage spray compositions containing, respectively, 100, 400 and 400 parts per million by weight of said compounds.

What is claimed is:

1. (Isothiocyanatomethoxy)-1,1'-biphenyl compounds corresponding to the formula

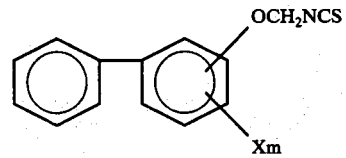

wherein
X represents, at each and every occurrence, Cl, Br, F, OCH₃, NO₂ or an alkyl group having from one to four carbon atoms, and
m is an integer having a value of 0, 1, 2, 3 or 4.

2. The compound of claim 1 which is 2-(isothiocyanatomethoxy)-1,1'-biphenyl.

3. The compound of claim 1 which is 3-(isothiocyanatomethoxy)-1,1'-biphenyl.

4. The compound of claim 1 which is 4-(isothiocyanatomethoxy)-1,1'-biphenyl.

5. The compound of claim 1 which is 2-chloro-4-(isothiocyanatomethoxy)-1,1'-biphenyl.

6. The compound of claim 1 which is 5-chloro-2-(isothiocyanatomethoxy)-1,1'-biphenyl.

7. The compound of claim 1 which is 3-methoxy-4-(isothiocyanatomethoxy)-1,1'-biphenyl.

8. The compound of claim 1 which is 2,6-dimethyl-4-(isothiocyanatomethoxy)-1,1'-biphenyl.

9. The compound of claim 1 which is 2-chloro-3-(isothiocyanatomethoxy)-1,1'-biphenyl.

10. The compound of claim 1 which is 2,6-dichloro-4-(isothiocyanatomethoxy)-1,1'-biphenyl.

11. The compound of claim 1 which is 2-ethyl-4-(isothiocyanatomethoxy)-1,1'-biphenyl.

12. The compound of claim 1 which is 2-fluoro-4-(isothiocyanatomethoxy)-1,1'-biphenyl.

13. The compound of claim 1 which is 2-bromo-4-(isothiocyanatomethoxy)-1,1'-biphenyl.

14. The compound of claim 1 which is 2-methyl-4-(isothiocyanatomethoxy)-1,1'-biphenyl.

15. The compound of claim 1 which is 2-methoxy-4-(isothiocyanatomethoxy)-1,1'-biphenyl.

* * * * *

UNITED STATES PATENT AND TRADEMARK OFFICE
CERTIFICATE OF CORRECTION

PATENT NO. : 4,067,896
DATED : January 10, 1978
INVENTOR(S) : James K. Pierce

It is certified that error appears in the above—identified patent and that said Letters Patent are hereby corrected as shown below:

Column 1, line 32 "having one" should read --having from one-- .

Signed and Sealed this

Tenth Day of October 1978

[SEAL]

Attest:

RUTH C. MASON
Attesting Officer

DONALD W. BANNER
Commissioner of Patents and Trademarks